United States Patent
Edwards

(10) Patent No.: US 7,998,159 B2
(45) Date of Patent: Aug. 16, 2011

(54) IRRIGATED CUTTING DEVICE

(75) Inventor: Kevin Cooper Edwards, Olive Branch, MS (US)

(73) Assignee: Gyrus Ent, L.L.C., Bartlett, TN (US)

( * ) Notice: Subject to any disclaimer, the term of this patent is extended or adjusted under 35 U.S.C. 154(b) by 966 days.

(21) Appl. No.: 11/976,288

(22) Filed: Oct. 23, 2007

(65) Prior Publication Data

US 2008/0114206 A1    May 15, 2008

Related U.S. Application Data

(60) Provisional application No. 60/858,952, filed on Nov. 15, 2006.

(51) Int. Cl.
*A61B 17/32* (2006.01)

(52) U.S. Cl. .......... 606/180; 606/169; 606/170

(58) Field of Classification Search ........... 606/167, 606/180, 168–171, 177, 79–85; 604/22, 604/19, 103.01, 103.02; 433/144–148; 600/562, 600/564, 566, 567

See application file for complete search history.

(56) References Cited

U.S. PATENT DOCUMENTS

| | | | | |
|---|---|---|---|---|
| 4,923,441 | A * | 5/1990 | Shuler | 604/22 |
| 5,411,514 | A * | 5/1995 | Fucci et al. | 606/180 |
| 5,759,185 | A * | 6/1998 | Grinberg | 606/80 |
| 6,068,641 | A | 5/2000 | Varsseveld | |
| 6,132,448 | A | 10/2000 | Perez et al. | |
| 6,293,957 | B1 | 9/2001 | Peters et al. | |
| 6,638,289 | B1 | 10/2003 | Johnson et al. | |
| 2003/0055404 | A1 * | 3/2003 | Moutafis | 604/540 |
| 2004/0230211 | A1 * | 11/2004 | Moutafis et al. | 606/167 |

\* cited by examiner

*Primary Examiner* — Todd E Manahan
*Assistant Examiner* — Amy Lang
(74) *Attorney, Agent, or Firm* — Oliff & Berridge PLC

(57) ABSTRACT

A cutting accessory for use with a powered surgical tool includes an elongated outer tube with an outer hub attached to the proximal end for releasably securing the cutting accessory within the powered tool. An elongated inner member is received within the outer tube and has an inner hub adapted to be driven by the surgical tool. The dimensions of the outer tube and inner member are such as to form an annular channel therebetween for the passage of irrigating fluid. The inner member carries a cutting tool, such as a burr, at its distal end, the tool being accessible through an aperture in the outer tube. A bearing member is located in the annular channel between the inner member and the outer tube, and a bypass channel runs external to the outer tube to carry irrigating fluid to the cutting tool bypassing the bearing member. An aperture through the outer tube connects the annular channel with the bypass channel.

12 Claims, 4 Drawing Sheets

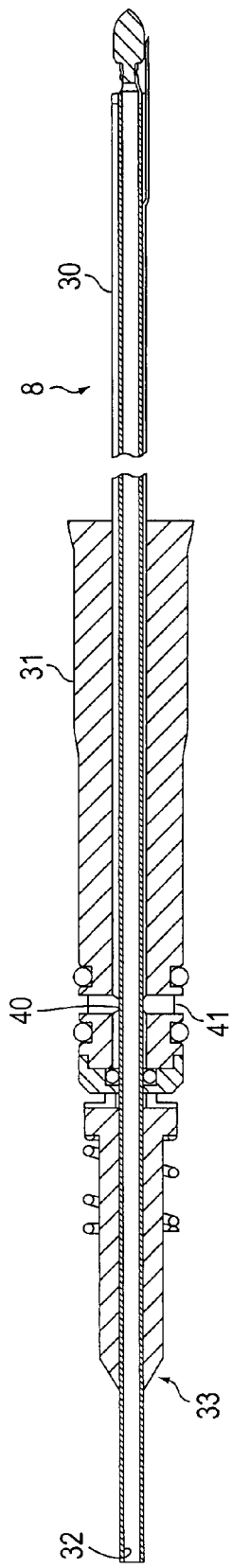
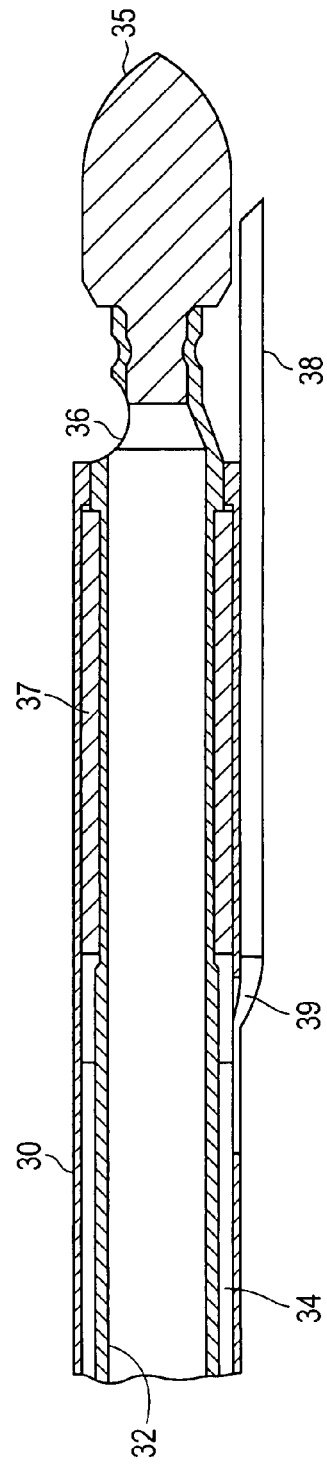
FIG. 2
FIG. 3

IRRIGATED CUTTING DEVICE

This nonprovisional application claims the benefit of U.S. Provisional Application No. 60/858,952, filed Nov. 15, 2006.

This invention relates to an irrigated cutting device such as a burr (or bur) used in an endoscopic cutting procedure such as sinus surgery.

Powered endoscopic surgery has now become readily accepted, and motorised handpieces are used with burr and shaver blades for a variety of endoscopic surgery, such as sinus, otologic, laryngeal and other surgery. The present invention relates to an irrigated burr blade for use in such surgery in connection with a motorised handpiece.

It has become standard practice to use the annular space between inner and outer elongate blade elements as the conduit for irrigating fluid. U.S. Pat. No. 6,293,957 describes the use of this annular space as a passage for irrigating fluid in sinus surgery. However, burr blades are designed for the cutting of harder materials, such as bone, and are often subjected to higher bending forces, leading to the need for a bearing element to support the cutting tool. Such a bearing element is often placed between the inner and outer blade elements, interrupting the fluid supply passage offered by the annular space. U.S. Pat. Nos. 6,068,641, 6,132,448 and 6,638,289 illustrate such bearing elements. The present invention attempts to provide an improved alternative to such irrigated cutting tools.

Accordingly, a cutting accessory for use with a powered surgical tool includes;

i) an elongated outer tube having a proximal end and a distal end;

ii) an outer hub attached to the proximal end of the outer tube, the outer hub being adapted to releasably secure the cutting accessory within the powered surgical tool;

iii) an elongated inner member received within the outer tube and having a proximal end and a distal end, the dimensions of the outer tube and the inner member being such as to form an annular channel therebetween for the passage of irrigating fluid;

iv) an inner hub attached to the proximal end of the inner member and adapted to be driven by the powered surgical tool;

v) a cutting tool carried by the distal end of the inner member, and accessible through an aperture in the region of the distal end of the outer tube;

vi) a bearing member located in the annular channel between the inner member and the outer tube, and blocking the annular channel towards the distal end of the inner member and the outer tube;

vii) a bypass channel running external to the outer tube and having a proximal end which is proximal to the bearing member and a distal end which is distal to the bearing member; and viii) an aperture through the outer tube connecting the annular channel and the bypass channel such that irrigating fluid introduced into the annular channel enters the bypass channel and exits the distal end of the bypass channel.

The bypass channel allows irrigating fluid introduced into the annular channel to bypass the bearing member and reach the distal end of the cutting accessory. It means that the bearing member can be a solid element, unlike for example in U.S. Pat. No. 6,068,641 in which the bearing member needs annular cut-outs in order to allow the passage of irrigating fluid.

Conveniently, the distal end of the bypass channel is adjacent the cutting tool, and in one arrangement is adapted to direct irrigating fluid on to the cutting tool. This can be achieved more effectively by means of an external bypass channel than by means of passages through the bearing member.

The inner member is typically a hollow tube, and includes a suction aperture towards the distal end thereof such that material can be moved under suction through the suction aperture and withdrawn through the inner member. In this way, irrigation can be provided to the surgical site, and the fluid is removed along with excised material through the hollow tube.

The outer tube conveniently includes an irrigation inlet aperture towards the proximal end thereof for introducing irrigation fluid into the annular channel between the inner member and the outer tube. The irrigation inlet aperture is conveniently in the region of the outer hub, and the outer hub has a corresponding aperture to allow irrigation fluid to pass through the outer hub and enter the annular channel.

The inner member conveniently includes a flexible portion, so that the cutting accessory can be formed as a curved blade. The flexible portion is typically formed of a wrapped material, helically wound to as to transfer torque to the cutting tool while bending within the curved blade. In this arrangement, the aperture through the outer tube connecting the annular channel and the bypass channel is conveniently located proximal to the flexible portion. This allows the fluid to bypass not only the bearing member but also the flexible portion, avoiding a longstanding problem where irrigation fluid passes through the wrap material of the flexible portion. To assist with diverting the fluid into the bypass channel, a fluid diversion member is conveniently provided to divert fluid through the aperture. This can be a seal such as an O-ring, or a baffle member to urge the fluid through the aperture into the bypass channel. In one convenient arrangement, the fluid diversion member is shrink tubing placed over the inner member downstream of the aperture.

The invention will now be described in more detail, by way of example only, with reference to the accompanying drawings, in which;

FIG. 2 is a schematic sectional view of a cutting blade assembly in accordance with the present invention;

FIG. 3 is an enlarged sectional view of a part of the cutting blade assembly of FIG. 2;

Figure 1:
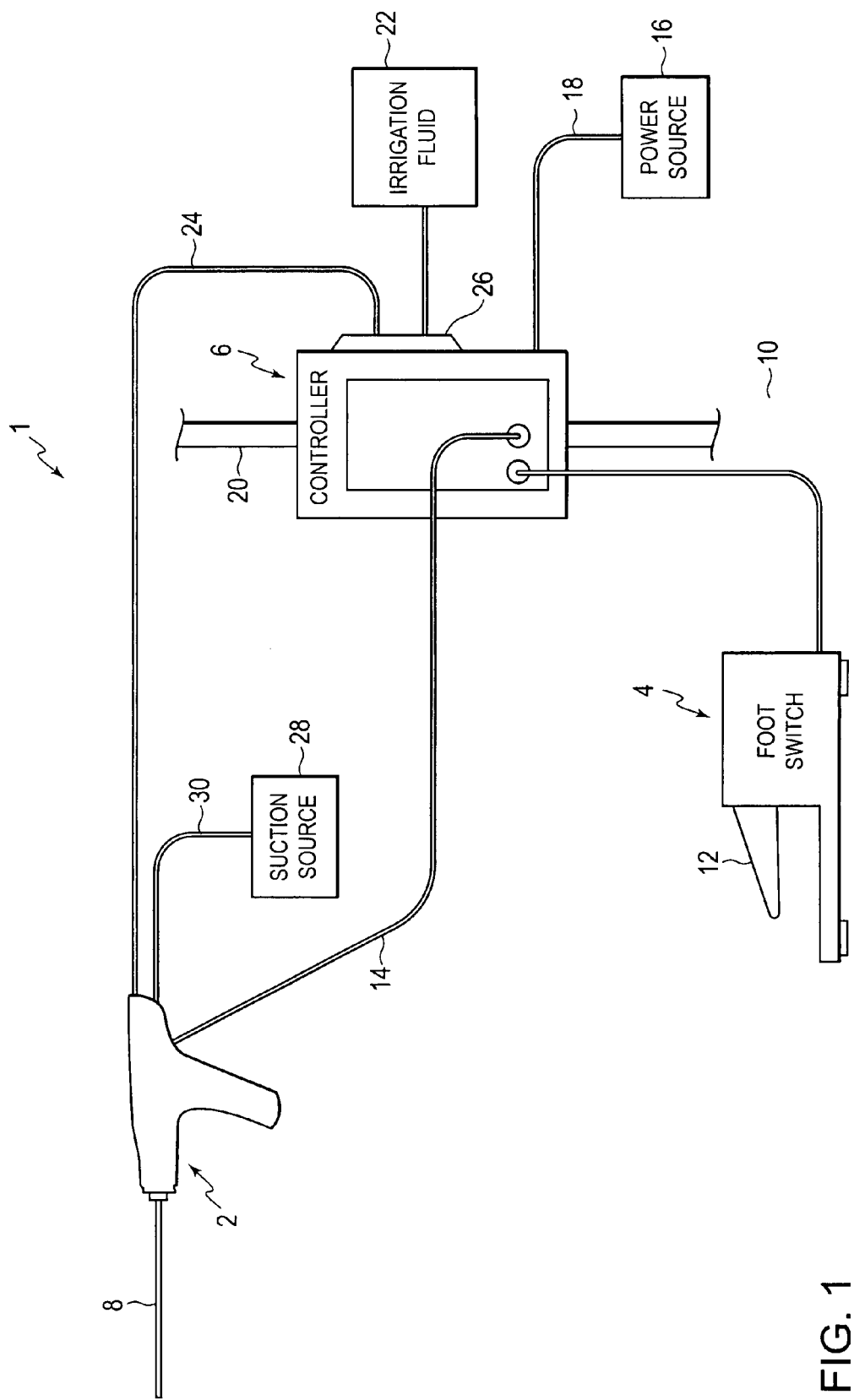
FIG. 1 is a schematic drawing of a powered endoscopic surgical system, in which a cutting blade assembly in accordance with the present invention can be used.

Referring to FIG. 1, there is shown an example of a powered surgical apparatus 1 used to operate a burr blade in accordance with the invention. As shown in FIG. 1, the apparatus 1 includes a handle 2, a footswitch 4 and a controller 6. A general description of these elements as well as their interrelationship is provided below.

The handle 2 includes a cutting blade assembly 8 at its distal end. The distal end of the cutting blade assembly 8 is usable to cut, shave and/or remove bodily material during a surgical procedure or operation. The distal end of the cutting blade assembly 8 can perform the cutting, shaving and/or removal in any manner, such as by rotation, for example. In operation, a surgeon grasps the handle 2 as if grasping a pistol and brings the distal end of the cutting blade assembly 8 into contact with the bodily material to be shaved, cut and/or removed.

The footswitch 4 is connected to the controller 6 via a footswitch signal line 10, such as an electric cable, for example. The footswitch 4 is typically disposed on the floor of a surgical room within reach of the surgeon's foot. The footswitch 4 includes an actuator member, such as a foot pedal 12, the actuation of which results in an input signal being transmitted to the controller 6 via the footswitch signal line 10. In operation, the surgeon places his or her foot on the footswitch 4 and depresses the foot pedal 12 to provide an input signal to the controller for the purpose of controlling at least one operation of the apparatus, such as energizing/de-energizing rotation of the cutting blade assembly 8, or speed of rotation of the cutting blade assembly 8, for example.

The controller 6 is also connected to the handle 2 via a handle signal line 14, such as an electric cable, for example. The controller 6 can output signals to the handle via the handle signal line 14, such as control signals controlling on/off status of the cutting blade assembly, and/or rotation speed of the cutting blade assembly 8 based upon input signals received by the controller 6 from the footswitch 4, for example.

The controller 6 is also connected to a power source 16 via a power source supply line 18, such as a standard electric cable or hospital grade power cord, for example. The controller 6 receives and utilizes a source of AC electric voltage from the power source 16.

As shown in FIG. 1, the controller 6 can be slideably disposed on a vertical rail 20. Slideably disposing the controller 6 on the vertical rail 20 enables the mounting height of the controller to adjusted to facilitate viewing data on the face of the controller, to take into account space constraints, or for any other purpose.

The handpiece can be connected to a source of irrigation fluid 22 by an irrigation fluid supply tube 24. The irrigation fluid can be provided to travel through the handle 2 and to the cutting blade assembly 8 and/or the surgical site for the purpose of lubricating the blade or blades for enhanced cutting or shaving efficiency, for example.

The handle 2 can also be connected to a source of suction 28 by a suction supply tube 30. The suction can be provided so as to extend through the handle 2 and to the cutting blade assembly 8 and/or the surgical site for the purpose or removing cut or shaven bodily material and/or irrigation fluid, for example.

Referring to FIGS. 2 and 3, a cutting blade assembly 8 is shown as comprising a hollow outer tube 30 having an outer hub 31 attached to its proximal end. Received within the outer tube 30 is an inner tubular member 32, with an inner hub 33 attached to its proximal end. In use, the outer hub 31 is received within the handle 2, and the inner hub 33 is driven for rotation by a motor (not shown) within the handle.

The dimensions of the inner member 32 and the outer tube 30 are such that an annular channel 34 is formed therebetween. A cutting tool in the form of a burr 35 is attached to the distal end of the inner member 32 and projects from the open distal end of the outer tube 30. A suction aperture 36 is provided in the inner member 32 towards the distal end thereof, giving access to the hollow interior of the tube.

As shown particularly in FIG. 3, a bearing sleeve 37 is provided at the distal end of the blade assembly 8, located in the annular channel 34 and blocking it accordingly. The bearing sleeve 37 is carried by the outer tube and serves to support the inner member when the cutting tool is subjected to lateral forces, for example when being pressed firmly against bone or other hard tissue to be abraded.

The distal end of the outer tube is also provided with an external bypass tube 38. This bypass tube runs along the outside of the outer tube 30, and has a proximal end just proximal of the bearing sleeve, and a distal end adjacent to the burr 35. An aperture 39 through the outer tube 30 connects the bypass tube 38 with the annular channel 34.

In use, irrigating fluid is supplied from the source 22 and fluid supply tube 24 to the handle 2. The irrigating fluid enters the annular channel 34 via an aperture 40 in the outer tube 30, and a circumferential recess 41 in the outer hub 31. The fluid passes down the annular channel 34 between the inner member 32 and the outer tube 30, until it reaches the bearing sleeve 37. The fluid then passes through the aperture 39 into the external bypass tube 38, and along the bypass tube before exiting adjacent the burr 35. In this way, the irrigating fluid is directed on to the burr 35, to provide the maximum cooling and irrigating effect. Excess fluid, as well as tissue and bone fragments cut by the burr 35, pass through the suction aperture 36 into the interior of the hollow member 32, and travel back up the cutting blade under the action of the suction source 28.

Figure 4:
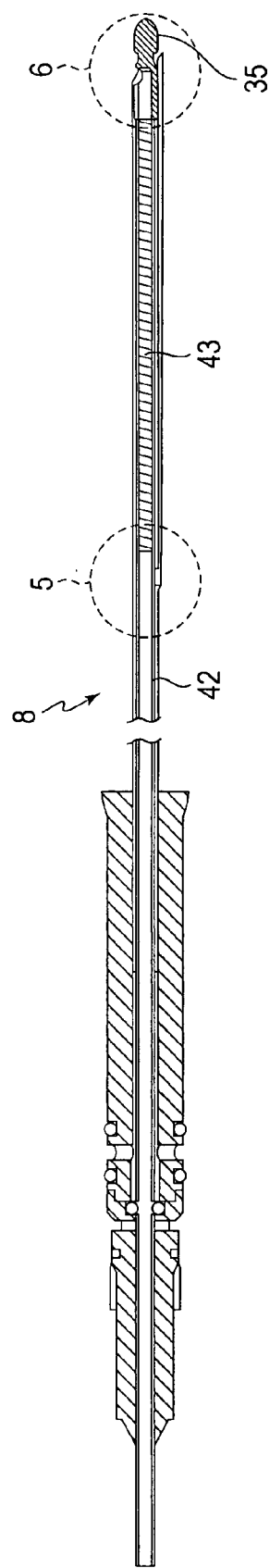
FIG. 4 is a schematic sectional view of a cutting blade assembly in accordance with an alternative embodiment of the present invention.
Figure 5:
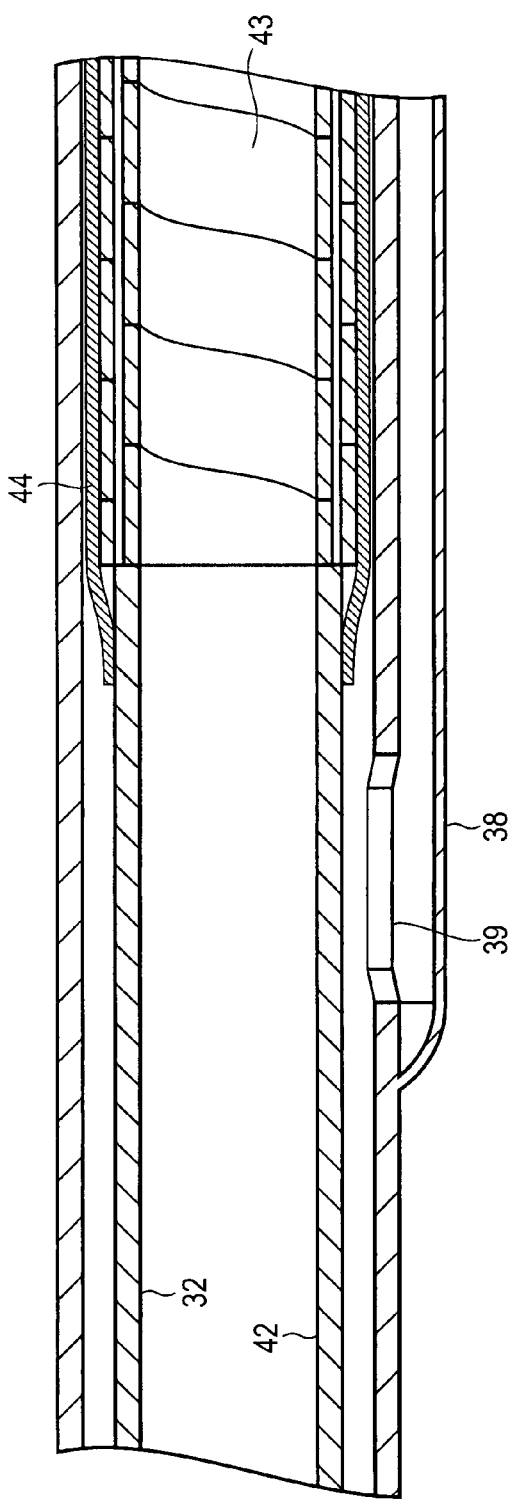
FIG. 5 is an enlarged view of the area A in FIG. 4.
Figure 6:
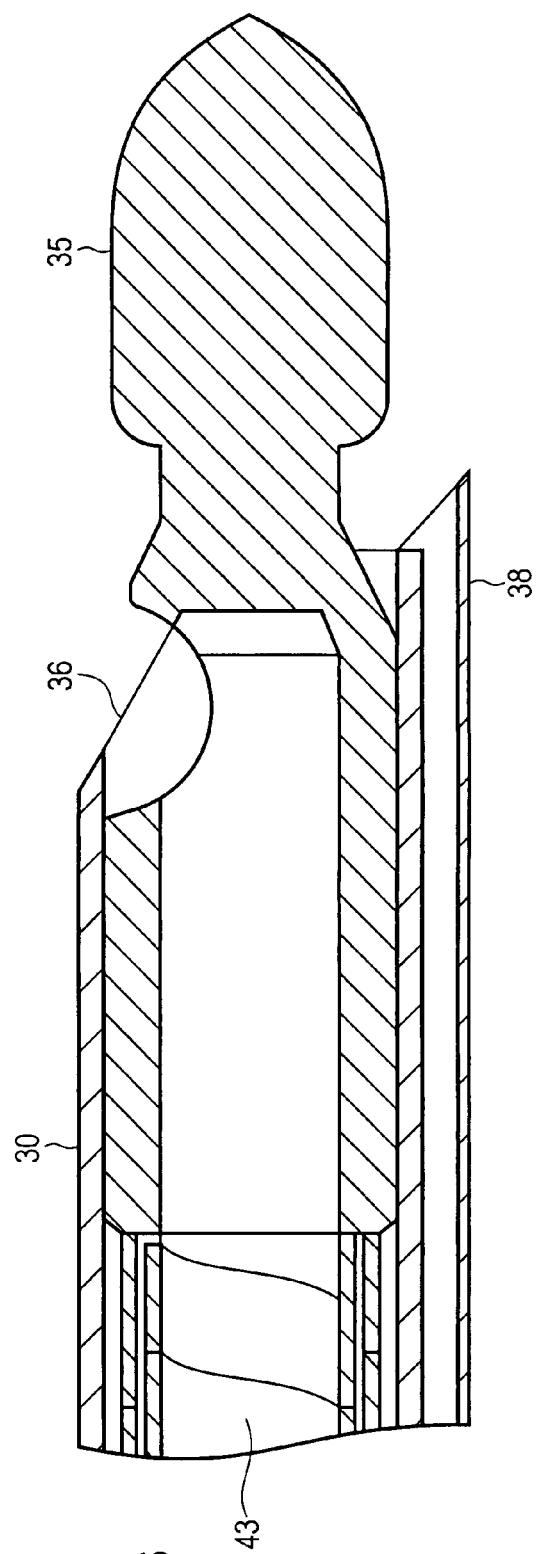
FIG. 6 is an enlarged view of the area B in FIG. 4.

FIGS. 4 to 6 show an alternative embodiment of cutting blade assembly 8, designed to be formed into a curved blade. The blade is substantially as previously described, with similar features designated by similar reference numerals. The inner member 32 is formed in three sections, with a rigid proximal section 42, a flexible intermediate section 43 and the distal cutting tool 35. The flexible intermediate section is formed of a helically wound wrap, typically of thin stainless steel material. This wrap section allows the intermediate section to bend, while continuing to transfer torque to the distal cutting element.

The bypass tube 38 is longer in the curved blade embodiment, and starts just proximal to the intermediate section 43, using an aperture 39 though the outer tube 30 as previously described. Shrink tubing 44 is provided at the transition between the proximal section 42 and intermediate section 43. This forces irrigating fluid through the aperture 39 as opposed to continuing in the annular channel 34 between the inner member 32 and outer tube 30. In this way, the irrigating fluid bypasses both the bearing sleeve 37 and the intermediate section 42, such that there is no problem with irrigating fluid passing through any gaps in the wrap material formed when the blade is bent.

The blade of FIGS. 4 to 6 is either bent to shape before being supplied to the user, or supplied straight and bent to the desired curved configuration by the user. The outer tube 30, along with the bypass tube 38, is bent to an angle typically between 15 and 40 degrees, but sometimes as much as 70 degrees or more. The flexible intermediate section 43 allows the inner member 32 to rotate within the outer tube 30, even though the outer tube is curved. The bypass tube adopts the curved shape of the blade, and continues to form a fluid channel as previously described, allowing irrigating fluid to be passed to the burr 35 directly and effectively.

This invention has been described herein in considerable detail in order to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention.

The invention claimed is:

1. A cutting accessory for use with a powered surgical tool, the cutting accessory including;
   i) an elongated outer tube having a proximal end and a distal end;

ii) an outer hub attached to the proximal end of the outer tube, the outer hub being adapted to releasably secure the cutting accessory within the powered surgical tool;

iii) an elongated inner member received within the outer tube and having a proximal end and a distal end, the dimensions of the outer tube and the inner member being such as to form an annular channel therebetween for the passage of irrigating fluid;

iv) an inner hub attached to the proximal end of the inner member and adapted to be driven by the powered surgical tool;

v) a cutting tool carried by the distal end of the inner member, and accessible through a first aperture in the region of the distal end of the outer tube;

vi) a bearing member located in the annular channel between the inner member and the outer tube, and blocking the annular channel towards the distal end of the inner member and the outer tube;

vii) a bypass channel running external to the outer tube and having a proximal end which is proximal to the bearing member and a distal end which is distal to the bearing member; and viii) a second aperture through the outer tube connecting the annular channel and the bypass channel such that irrigating fluid introduced into the annular channel enters the bypass channel and exits the distal end of the bypass channel, wherein the second aperture is proximal to the distal bearing member.

2. A cutting accessory according to claim 1 wherein the distal end of the bypass channel is adjacent the cutting tool.

3. A cutting accessory according to claim 2 wherein the distal end of the bypass channel is adapted to direct irrigating fluid on to the cutting tool.

4. A cutting accessory according to claim 1 wherein the bearing member is a bearing sleeve carried by the outer tube.

5. A cutting accessory according to claim 1 wherein the inner member is a hollow tube.

6. A cutting accessory according to claim 5 wherein the inner member includes a suction aperture towards the distal end thereof such that material can be moved under suction through the suction aperture and withdrawn through the inner member.

7. A cutting accessory according to claim 1 wherein the outer tube includes an irrigation inlet aperture towards the proximal end thereof for introducing irrigation fluid into the annular channel between the inner member and the outer tube.

8. A cutting accessory according to claim 7 wherein the irrigation inlet aperture is in the region of the outer hub, and the outer hub has a corresponding aperture to allow irrigation fluid to pass through the outer hub and enter the annular channel.

9. A cutting accessory according to claim 1 wherein the inner member includes a flexible portion.

10. A cutting accessory according to claim 9 wherein second aperture through the outer tube connecting the annular channel and the bypass channel is located proximal to the flexible portion.

11. A cutting accessory according to claim 10 wherein a fluid diversion member is provided to divert fluid through second aperture.

12. A cutting accessory according to claim 1, wherein the second aperture is disposed between the bearing member and the proximal end of the outer tube.

* * * * *